Figure 3:
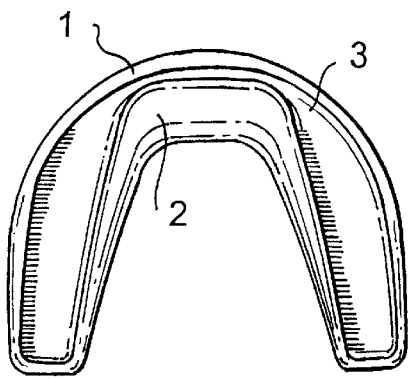

United States Patent
Mathieu

Patent Number: 6,132,208
Date of Patent: Oct. 17, 2000

[54] BRACES FOR DENTIFACIAL FUNCTIONAL ORTHOPAEDIC AND PERIODONTAL TREATMENT

[75] Inventor: Rodrigue Mathieu, Montpellier, France

[73] Assignee: Sodisapf, Montpellier, France

[21] Appl. No.: 09/230,657

[22] PCT Filed: Jul. 29, 1997

[86] PCT No.: PCT/FR97/01416

§ 371 Date: May 20, 1999

§ 102(e) Date: May 20, 1999

[87] PCT Pub. No.: WO98/04207

PCT Pub. Date: Feb. 5, 1998

[30] Foreign Application Priority Data

Jul. 30, 1996 [FR] France .................................. 96 09837

[51] Int. Cl.[7] .................................................... A61C 7/08
[52] U.S. Cl. ................................................ 433/6; 128/861
[58] Field of Search ........................ 433/6, 140; 128/861, 128/862

[56] References Cited

U.S. PATENT DOCUMENTS 3,478,429  11/1969  Shilliday ........................... 433/6
5,876,199   3/1999  Bergersen ......................... 433/6

FOREIGN PATENT DOCUMENTS 2 641 964  7/1990  France .
2 279 876  1/1995  United Kingdom .

*Primary Examiner*—Ralph A. Lewis
*Attorney, Agent, or Firm*—Steven J. Moore; Cummings & Lockwood

[57] ABSTRACT

Braces for dentifacial functional orthopaedic and periodontal treatment made of natural or synthetic, flexible, food-grade material, generally consisting of a double cradle (or trough), these two cradles having externally, in a plane, a flaring U-shape and separated by a thick horizontal partition (3). The braces are further characterised in that: (a) the portion of the cradle designed for receiving the lower incisors is sufficient for fitting in the lower four incisors; (c) the height of the side lingual (2) and vestibular (1) partitions defining the channel designed for receiving the lower incisors (4), from the thick horizontal partition (3), is at least equal to the height of the incisors up to their neck.

11 Claims, 3 Drawing Sheets

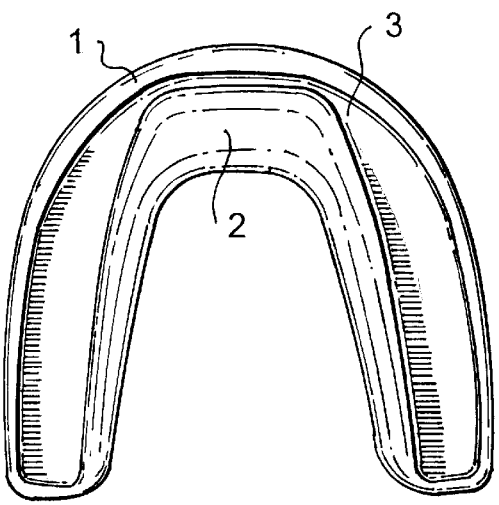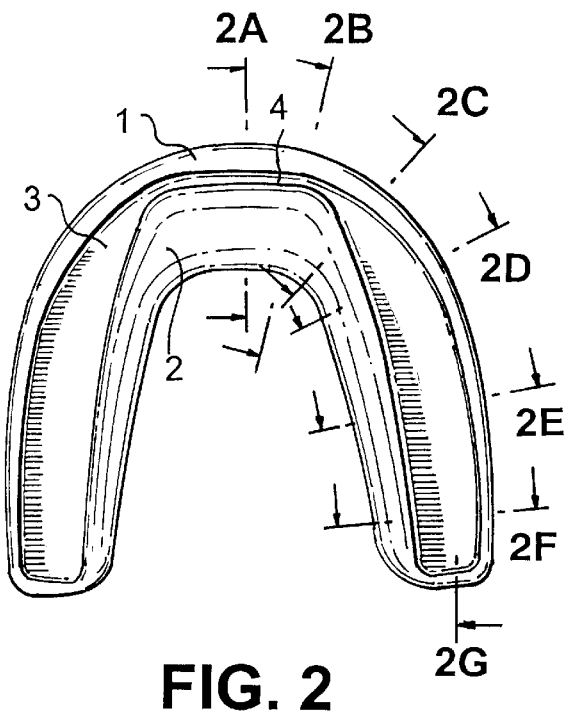
FIG. 1
FIG. 2
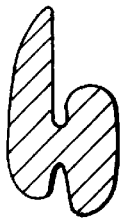
FIG. 2A  FIG. 2B  FIG. 2C
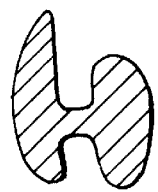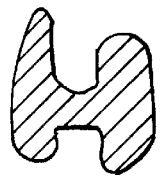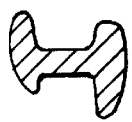
FIG. 2D  FIG. 2E  FIG. 2F
FIG. 2G

BRACES FOR DENTIFACIAL FUNCTIONAL ORTHOPAEDIC AND PERIODONTAL TREATMENT

BACKGROUND OF THE INVENTION

1. Field of the Invention

The subject of the present invention is medical appliances for functional dento-facial orthopaedic treatment and periodontics, aimed at correcting functional disorders with neurovegetative functions, more particularly functional disorders with:

nasal breathing, mastication, swallowing, phonation, and consequently aimed at correcting anomalies in the shape of the mouth, that is to say anomalies in the shape of the buccal osseous bases and malpositions of the teeth.

2. Background of the Related Art

In order to correct the position of the teeth in patients, it is known practice to employ corrective medical appliances known as "orthodontic positioners", which in plan view adopt the shape of the U and comprise at least one upper or lower trough but normally both an upper and a lower trough, each trough containing a number of depressions for receiving and retaining the teeth held therein and returning them to a position that is estimated as being the ideal position. There are various kinds of orthodontic positioner, what they have in common being that they have specific locations for the existing teeth and, in some cases, for the permanent teeth yet to come (see, for example, French Patent No. 2329247): movements of the teeth within these orthodontic positioners are therefore not permitted.

Devices known by the name of "channel activators" for treatment as part of dento-facial therapy are also known, from French Patent No. 2641964.

These channel activators consist, in general, of a double tray (or double trough) of semi-elliptical shape, the channels or troughs being separated by a horizontal partition (or thickness). Unlike in the aforementioned orthodontic positioners, there are no precise receivings for the teeth within the double channel. Indeed, the interior surface of the vertical or inclined walls of the double channel, among which the vestibular strip (external) and the lingual strip (internal), and the surface of the horizontal partition, are smooth.

The basic idea underlying the channel activators described in French Patent No. 2641964 is as follows: buccal deformation and the accompanying malpositions of the teeth are due to functional disorders with the neurovegetative functions that are: nasal breathing, mastication, swallowing and phonation. In most cases treated, the wearing of the tray activators and the exercises that accompany their day-to-day wearing allow the four aforementioned neurovegetative functions to be corrected and as a consequence allow the anomalies in the shape of the buccal osseous bases and malpositions of the teeth to be corrected.

However, the channel activators described in French Patent No. 2641964 are not entirely satisfactory as they actually present the following drawbacks:

in some instances it has been found, during treatment, that an incisor infraclusion (or gap) appears. In other words, a space in the vertical direction appears between the upper and lower incisors. This infraclusion is due, in particular, to the position of the tongue, this position being associated with atypical swallowing of a child-like type (inserting the tongue) between the incisors at the time of swallowing;

in other instances, the transverse expansion that is sought and needed for fitting in all the teeth is not achieved;

in the case of the treatment of certain adults, certain anomalies in the shape of the buccal osseous bases could not be corrected, such as:

a significant MDM (Maxillo-Dental Malocclusion) corresponding to teeth which are too large compared with the size of the jaw bones [(i.e. the upper jaw (maxilla) and the lower jaw (mandible)];

an hereditary class-III anomaly (or prognathism) corresponding to a forward position of the mandible, often associated with underdevelopment of the upper jaw bone.

An essential objective of the invention is therefore to provide a solution to the aforementioned drawbacks of the channel activators described in French Patent No. 2641964. Another important objective of the invention is to provide new corrective appliances for functional dento-facial orthopaedic treatments which are suitable for and effective in treating children who have their deciduous or permanent incisors, as well as adolescents and adults, in whom the risks of a relapse or of the appearance of further malpositions of the teeth in normal use of these appliances are minimized.

SUMMARY OF THE INVENTION

To this end, the subject of the present invention is novel corrective appliances for functional dento-facial orthopaedic treatment and periodontics, made of a natural or synthetic flexible and food-grade material, consisting, in general, of a double channel (or trough), these two channel externally, in a horizontal plane, adopting the shape of a flared U and being separated by a thick, slightly horizontal, partition, the interior surface of these two trays, which are defined between, on the one hand, lateral walls, among which the vestibular strip (external) and the lingual and palatine strips or rolls (internal) and, on the other hand, the thick horizontal partition, being smooth.

The novel corrective appliances for functional dento-facial orthopaedic treatment and periodontics according to the invention are characterized in that:

(a) that part of the tray that is intended to receive the lower incisors is in the shape of a straight channel which opens, at its two ends, into two tooth channels respectively, these being intended to receive respectively a lower canine, two lower premolars (corresponding to two milk-tooth molars of a child) and, possibly, at least one lower molar;

(b) the length of the straight channel is designed to be long enough for the four lower incisors to have enough space to fit in it;

(c) the depth of the straight channel is designed to completely enclose the lower incisors and, for this purpose, the height of the lingual and vestibular side walls delimiting the straight channel from the thick horizontal partition is at least equal to the height of the incisors up to their neck.

In an attempt at simplifying matters, the medical appliances for functional dento-facial orthopaedic treatment and periodontics of the present invention will hereafter be called "corrective appliances".

In the context of the invention:

the term "lingual (side) wall" or "lingual strip" or "lingual roll" denotes that part of the corrective appliances which runs alongside the lower teeth on the tongue side, in the region of the incisors, as well as the canine, the premolars (or milk-tooth premolars in the case of a child) and the molars;

the term "palatine (side) wall" or "palatine strip" denotes the internal wall of the corrective appliances on the upper teeth and palate side;

the term "vestibular (side) wall" or "vestibular strip" denotes the outer wall of the corrective appliances located on the lower and upper teeth side;

the word "flexible", used to qualify the corrective appliances according to the invention, means that these appliances have an elastic behaviour when worn in the mouth and during chewing exercises performed in the course of treatment. Because of this elastic behaviour, the corrective appliances according to the invention have a toning effect and stimulate the facial and buccal muscles in the course of chewing exercises.

the quantified values given to the thickness of the vestibular, lingual and palatine side walls, quoted in what follows of the description, are measured slightly mid-way up these walls.

Advantageously, the corrective appliances according to the present invention are appliances of standardized shapes and sizes according to the age of the patient and the anomaly (or anomalies) in shape that is (are) to be treated. They are prefabricated from a natural or synthetic material that meets the requirements set down in French and European standards regarding the plastics intended for contact with food and which are sufficiently flexible. Furthermore, it has to be possible, with the chosen material, for the corrective appliance to be worn in the mouth without any appreciable loss in effectiveness or damage to it when subjected to chewing forces over a reasonable period of time. In this respect, the corrective appliances need to be replaced regularly, about every two to three months, for reasons of lessening of effectiveness as their toning effect becomes insufficient and for reasons of hygiene. Preferably, the corrective appliances according to the invention are based on flexible rubber, preferably on vulcanized flexible rubber so that they keep better in the mouth.

Advantageously too, the material of which the corrective appliances of the invention are made is flavoured like chewing gums.

A first important feature of the corrective appliances according to the preferred embodiment of the present invention lies in the fact that that part of the double channel receiving the lower incisors is a straight or rectilinear channel, each end of this straight channel ending in a tooth channel intended to receive the lower canine, the two lower premolars (or the corresponding two milk-tooth molars) and, possibly, at least one lower molar. Consequently, in horizontal section, the straight tooth channel is essentially represented by two parallel straight lines.

By contrast, the channel activators described in French Patent No. 2641964 have a markedly rounded shape in the region of the lower incisors, involving a curvature of the channel that receives the lower incisors, such that the distance separating the middle of the arc, corresponding to the intersection of a horizontal plane with the vestibular internal side wall of the channel of limited curvature receiving the lower incisors, and the middle of the segment of straight line passing through the ends of the arc is at least equal to 3 mm or more.

The tooth channel receiving the lower incisors is delimited by two smooth side walls, of vertical or inclined overall shape, which are the lower vestibular strip and the lingual strip (or roll).

The internal lingual side wall of the tooth channel receiving the lower incisors is extended at its two ends by the internal lingual side walls of the two tooth channels intended to receive the lower canine, the two lower premolars (or the corresponding two milk-tooth molars) and possibly at least one lower molar, so that in horizontal section, these three lateral walls form a "U" with flared legs.

Advantageously, the width of the channel, which is preferably straight, in its upper part (i.e. near to the slightly horizontal thick partition), is designed to be slightly equal to the thickness of the lower incisors in the region of the neck, in the sagittal direction (i.e. in the plane of symmetry passing through the middle of these incisors).

Likewise, the width of the tooth channel intended to receive the upper incisors is advantageously designed, at its upper part, to be slightly equal to the thickness of the lower incisors in the region of the neck, in the sagittal direction.

According to a second important feature of the invention, the length of the tooth channel receiving the lower incisors, which is preferably rectilinear, is designed to be long enough that the four lower incisors have enough space to fit in it:

in the case of a patient who has his deciduous lower incisors, that is to say between about the age of 3 and up to about the age of 6 or above, the length of this channel is of the order of 20 mm±2 mm;

in the case of a patient who has lost his deciduous lower incisors and has not yet got his permanent lower incisors, the length of this channel is of the order of 22 mm±2 mm;

in the case of a patient who has got his permanent lower incisors, that is to say generally from about the age of 6 or above, the length of this channel is of the order of 24 mm±1 mm.

Likewise, the tooth channel intended to receive the upper incisors, which is slightly rounded, is designed to be large enough that the upper incisors have enough space to fit in it. To achieve this, that part of the tooth channel that is intended to receive the upper incisors is preferably laterally delimited by a vestibular wall, somewhat vertical and slightly curved, in the transverse direction (from left to right or vice versa) and a palatine wall which overall is rounded in shape in the anterio-posterior direction (from front to back or vice versa) and slightly curved in the transverse direction.

According to a third important feature of the invention, the depth of the channel receiving the lower incisors, which is preferably straight, is such that this channel can surround the lower incisors, at least as far as their neck, when worn in the mouth, with teeth clenched. Also as a preference, the depth of this channel measured from the thick horizontal partition does not exceed the height of the lower incisors from their cutting edge down to their neck. Also, the depth of the tooth channel intended to receive the upper incisors is designed to be great enough to allow it to surround the upper incisors at least as far as their neck, when worn in the mouth with the teeth clenched. Also as a preference, the dimensions of the tooth channel intended to receive the upper incisors are designed to allow:

the upper maxillar arch to be surrounded as far as the boundary between the gum and the inner lip, without resting on the mucosa so as not to injure them;

slight pressure to be exerted on the palate.

In the event of serious discomfort or injury when the appliance is worn in the mouth, the height of the (lower and/or upper) vestibular wall and/or the height of the lingual wall and/or the height of the palatine wall may be reduced.

Furthermore, that portion of the thick horizontal partition on which the lower and upper incisors rest is designed to be planar so that all the incisors rest at the same time against the thick horizontal partition and all receive the same stimulation.

Thanks to the very limited curvature of the tooth channel receiving the lower incisors, which is preferably straight (or rectilinear) (feature (a) of the invention) and to its dimensions designed to suit the incisors present (features (b) and (c) of the invention), the lower incisors can no longer be rounded or vestibularized (i.e. incisors which slope forwards): therefore, the number of incisor infraclusions observed in young patients has been considerably reduced.

Furthermore, thanks to such a tooth channel, which is preferably rectilinear in the region of the lower incisors, the novel corrective appliances are more effective in correcting the four neurovegetative functions mentioned earlier. Thus, the presence of a tooth channel, which is of very limited curvature, and preferably rectilinear in the region of the lower incisors, allows better correction of the position of the tongue (and therefore of swallowing) and consequently allows better correction of the other neurovegetative functions and a better correction of the anomalies in the shape of the buccal osseous bases and of the corresponding malpositions of the teeth.

Another advantage of the invention lies in the long-term stability of the corrections achieved.

With the exception of the length of the channels receiving the upper and lower incisors, the other dimensions of the corrective appliances according to the invention can vary according to the age of the patient to be treated, the size of the patient's mouth and the pathology to be treated. It is thus possible to vary:

the length and depth of the tooth channels receiving the canines, the premolars and, possibly, at least one molar;

the thicknesses of the vestibular, lingual and palatine walls, these thicknesses advantageously being at least equal to 2 mm; the greatest thicknesses are reached by the lingual and palatine walls with corrective appliances that are aimed at transversely expanding the jaw bones;

the thickness of the horizontal partition, which is preferably greater in the region of the incisors than the thickness of this same horizontal partition in the region of the other teeth, this being with a view to enjoying a greater toning effect at this point and thus increasing the pressures and therefore stimulations given to the incisors. In the region of the Advantageously too, the material of which the corrective appliances of the invention are made is flavoured like chewing gums.

A first important feature of the corrective appliances according to the present invention lies in the fact that that part of the double tray receiving the lower incisors is a straight or rectilinear channel, each end of this straight channel ending in a tooth channel intended to receive the lower canine, the two lower premolars (or the corresponding two milk-tooth molars) and, possibly, at least one lower molar. Consequently, in horizontal section, the straight tooth channel is essentially represented by two parallel straight lines.

By contrast, the tray activators described in French Patent No. 2641964 have a markedly rounded shape in the region of the lower incisors, involving a curvature of the channel that receives the lower incisors, such that the distance separating the middle of the arc, corresponding to the intersection of a horizontal plane with the vestibular internal side wall of the channel of limited curvature receiving the lower incisors, and the middle of the segment of straight line passing through the ends of the arc is at least equal to 3 mm or more.

The tooth channel receiving the lower incisors is delimited by two smooth side walls, of vertical or inclined overall shape, which are the lower vestibular strip and the lingual strip (or roll).

The internal lingual side wall of the tooth channel receiving the lower incisors is extended at its two ends by the internal lingual side walls of the two tooth channels intended to receive the lower canine, the two lower premolars (or the corresponding two milk-tooth molars) and possibly at least one lower molar, so that in horizontal section, these three lateral walls form a "U" with flared legs.

Advantageously, the width of the straight channel, in its upper part (i.e. near to the slightly horizontal thick partition), is designed to be slightly equal to the thickness of the lower incisors in the region of the neck, in the sagittal direction (i.e. in the plane of symmetry passing through the middle of these incisors).

Likewise, the width of the tooth channel intended to receive the upper incisors is advantageously designed, at its upper part, to be slightly equal to the thickness of the lower incisors in the region of the neck, in the sagittal direction.

According to a second important feature of the invention, the length of the tooth channel receiving the lower incisors is designed to be long enough that the four lower incisors have enough space to fit in it:

in the case of a patient who has his deciduous lower incisors, that is to say between about the age of 3 and up to about the age of 6 or above, the length of this channel is of the order of 20 mm±2 mm;

in the case of a patient who has lost his deciduous lower incisors and has not yet got his permanent lower incisors, the length of this channel is of the order of 22 mm±2 mm;

in the case of a patient who has got his permanent lower incisors, that is to say generally from about the age of 6 or above, the length of this channel is of the order of 24 mm±1 mm.

Likewise, the tooth channel intended to receive the upper incisors, which is slightly rounded, is designed to be large enough that the upper incisors have enough space to fit in it. To achieve this, that part of the tooth channel that is intended to receive the upper incisors is preferably laterally delimited by a vestibular wall, somewhat vertical and slightly curved, in the transverse direction (from left to right or vice versa) and a palatine wall which overall is rounded in shape in the anterio-posterior direction (from front to back or vice versa) and slightly curved in the transverse direction.

According to a third important feature of the invention, the depth of the channel receiving the lower incisors, which is straight, is such that this channel can surround the lower incisors, at least as far as their neck, when worn in the mouth, with teeth clenched. Also as a preference, the depth of this channel measured from the thick horizontal partition does not exceed the height of the lower incisors from their cutting edge down to their neck. Also, the depth of the tooth channel intended to receive the upper incisors is designed to be great enough to allow it to surround the upper incisors at least as far as their neck, when worn in the mouth with the teeth clenched. Also as a preference, the dimensions of the tooth channel intended to receive the upper incisors are designed to allow:

the upper maxillar arch to be surrounded as far as the boundary between the gum and the inner lip, without resting on the mucosa so as not to injure them;

slight pressure to be exerted on the palate.

In the event of serious discomfort or injury when the appliance is worn in the mouth, the height of the (lower and/or upper) vestibular wall and/or the height of the lingual wall and/or the height of the palatine wall may be reduced.

Furthermore, that portion of the thick horizontal partition on which the lower and upper incisors rest is designed to be planar so that all the incisors rest at the same time against the thick horizontal partition and all receive the same stimulation.

Thanks to the tooth channel receiving the lower incisors, which is straight (or rectilinear) (feature (a) of the invention) and to its dimensions designed to suit the incisors present (features (b) and (c) of the invention), the lower incisors can no longer be rounded or vestibularized (i.e. incisors which slope forwards): therefore, the number of incisor infraclusions observed in young patients has been considerably reduced.

Furthermore, thanks to such a tooth channel, which is rectilinear in the region of the lower incisors, the novel corrective appliances are more effective in correcting the four neurovegetative functions mentioned earlier. Thus, the presence of a tooth channel, rectilinear in the region of the lower incisors, allows better correction of the position of the tongue (and therefore of swallowing) and consequently allows better correction of the other neurovegetative functions and a better correction of the anomalies in the shape of the buccal osseous bases and of the corresponding malpositions of the teeth.

Another advantage of the invention lies in the long-term stability of the corrections achieved.

With the exception of the length of the channels receiving the upper and lower incisors, the other dimensions of the corrective appliances according to the invention can vary according to the age of the patient to be treated, the size of the patient's mouth and the pathology to be treated. It is thus possible to vary:

the length and depth of the tooth channels receiving the canines, the premolars and, possibly, at least one molar;

the thicknesses of the vestibular, lingual and palatine walls, these thicknesses advantageously being at least equal to 2 mm; the greatest thicknesses are reached by the lingual and palatine walls with corrective appliances that are aimed at transversely expanding the jaw bones;

the thickness of the horizontal partition, which is preferably greater in the region of the incisors than the thickness of this same horizontal partition in the region of the other teeth, this being with a view to enjoying a greater toning effect at this point and thus increasing the pressures and therefore stimulations given to the incisors. In the region of the incisors, the thickness of the horizontal partition is preferably between 2 and 5 mm;

in general, the external dimensions of the corrective appliances.

The main action of the lingual, palatine and vestibular walls is to correct an inclined implantation to a slightly vertical implantation. Likewise, in the case of corrective appliances for transverse expansion, a second major action of the lingual and palatine walls is to make space and to part the teeth.

Advantageously, the lingual wall (or lingual roll), which corresponds to that part of the appliance which runs alongside the lower teeth on the tongue side in the region of the incisors, as well as the canine, the premolars and the molars is designed to be:

tall enough to cover the teeth and the alveolar bone in part without reaching the frenum of the tongue;

thick enough to allow, in certain instances, the transverse expansion needed to provide space for all the teeth.

Furthermore, in order to encourage or to maintain a vertical implantation of the lower incisors, the thickness of the lingual wall is advantageously greater in the region of the lower incisors than it is in the region of the other lower teeth. In general, the thickness of the lingual wall in the region of the lower incisors varies, according to the age of the patient, between 3±1 mm and 7±1 mm, while the thickness of the lingual wall in the region of the molars varies between 2±1 mm and 4±1 mm. Likewise, the thickness of the palatine wall in the region of the upper incisors is greater than the thickness of the palatine wall in the region of the other teeth. In general the thickness of the palatine wall in the region of the upper incisors varies, according to the age of the patient, between 4±1 mm and 10±1 mm; while the thickness of the palatine wall in the region of the molars varies between 3±1 mm and 5±1 mm.

The corrective appliances according to the invention are recommended for treating children (from the age of about 3) as soon as they have their milk-tooth incisors or permanent incisors, adolescents and adults (who may be over 50). By contrast, the positioners of the prior art cannot generally be envisaged until the first permanent teeth come through, namely from the age of about 6.

The functional corrective appliances according to the present invention make it possible to treat:

At the same time, by following the aforementioned exercises normally, the corrective appliances according to the invention make it possible, in the majority of cases, under the aforementioned provisos, gradually to correct the four neurovegetative functions which are functionally interdependent and to derive the greatest benefit from the anticipated results.

Thus it becomes possible to correct functional disorders of the neurovegetative functions and the resulting anomalies in the shape of the mouth.

Finally, it is important to note that, in addition to the aforementioned advantages, the corrective appliances according to the invention have the advantages of the tray activators described in French Patent No. 2641964 without the drawbacks mentioned earlier.

The invention will now be illustrated through three particular embodiments of the invention.

On plate 1/3, in FIGS. 1 and 2, are depicted two views from above and below of a corrective appliance for transverse expansion, which appliance is intended for an adult, these two views from above and below corresponding respectively to the tray for the upper jaw (FIG. 1) and the tray for the lower jaw (FIG. 2). The upper and lower trays are also specified by means of cross sections A-G.

Figure 4:
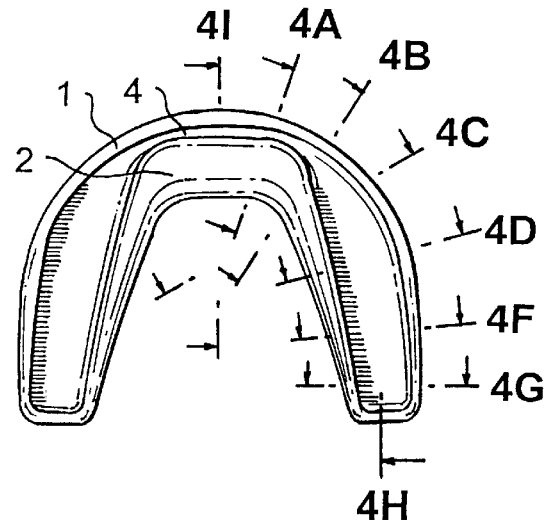
Figure 4A:
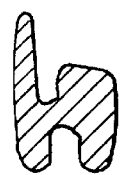
Figure 4B:
Figure 4C:
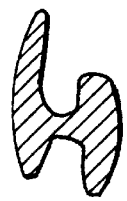
Figure 4D:
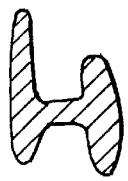
Figure 4F:
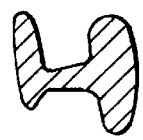
Figure 4G:
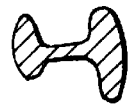
Figure 4H:
Figure 4I:

On plate 2/3, in FIGS. 3 and 4, are depicted two views from above and below of a corrective appliance for transverse expansion, intended for a child of between about 6 and about 12, these two views from above and below corresponding respectively to the tray for the upper jaw (FIG. 3) and to the tray for the lower jaw (FIG. 4). The upper and lower trays are further specified by means of cross sections I-H.

Figure 5:
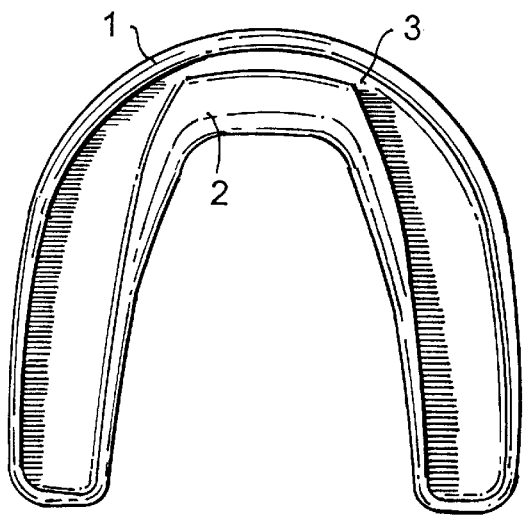
Figure 6:
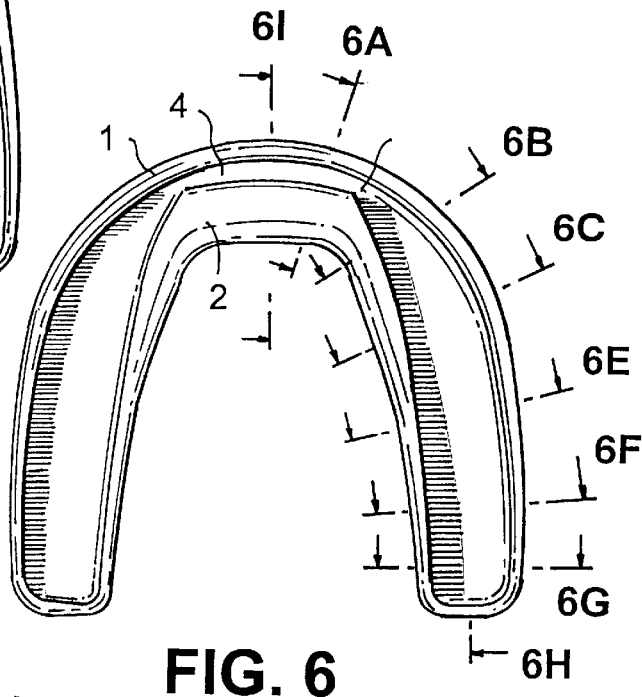
Figure 6A:
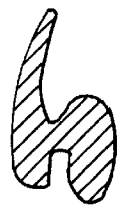
Figure 6B:
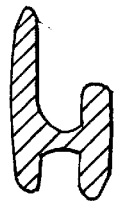
Figure 6C:
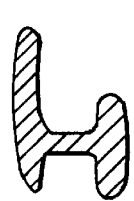
Figure 6E:
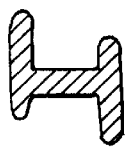
Figure 6F:
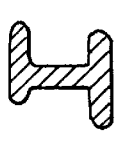
Figure 6G:
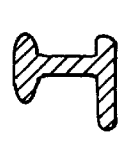
Figure 6H:
Figure 6I:

On plate 3/3, in FIGS. 5 and 6, are depicted two views from above and below of a shaping corrective appliance, intended for an adult, these two views from above and below corresponding respectively to the tray for the upper jaw (FIG. 5) and to the tray for the lower jaw (FIG. 6). The upper and lower trays are further specified by means of cross sections I-H.

As can be seen in FIGS. 1 and 2, the corrective appliance for transverse expansion consists of two vertical strips (1, 2) connected by a thick horizontal partition (3). The cross sections A-G show the overall shape of the upper and lower trays. These trays are also sized to cover the maxillar and mandibular arches as far as the neck. The rectilinear tooth channel (4) intended to receive the lower incisors is 24 mm long because this corrective appliance is intended for an adult.

The main action of the corrective appliance for transverse expansion is to correct an MDM.

Like all the corrective appliances according to the invention, the appliance described in plate I/3 is designed to free, incite and guide the impulses produced by the sets of muscles. Furthermore, this appliance is designed to increase the dimensions of the osseous bases in the jaw bones region and, if necessary, to increase the dimensions of the alveoli. This appliance is also designed to allow the implantation of the teeth to be normalized, and to allow good occlusion and correct and functional dental articulation. To this end, by comparison with the shaping corrective appliance shown in FIGS. 5 and 6, this appliance is characterized by:

- a greater thickness of the vestibular strip (of the order of 4 mm in the region of the lower incisors and of the order of 5 mm in the region of the upper incisors—(see sections A and B);
- far greater thickness of the lingual strip (internal) which, in addition, is extended more downwards than in the shaping corrective appliance for encouraging a widening of the mandible;
- greater width of the tooth corridor bounded between the two (lingual and vestibular) strips, to allow centrifugal moving of the teeth.

The corrective appliance depicted in FIGS. 3 and 4 is also aimed at transverse expansion, but in patients aged from about 6 to 12. This appliance consists of two vertical strips (1, 2) connected by a thick horizontal partition (3). The cross sections I-H show the overall shape of the upper and lower channel. These two trays are dimensioned to cover the mandibular arch as far as the neck and the maxillar arch as far as the vestibule. The rectilinear tooth channel (4) intended to receive the lower incisors is of the order of 24 mm long if the patient has his permanent incisors or is shorter than this (on this point, please refer to the description of the invention).

This corrective appliance for transverse expansion has the same features as the appliance depicted in FIGS. 1 and 2, the only differences lying in the external dimensions of the appliance and in the thicknesses of these walls which are smaller, to allow it to be worn in the mouth of a child 6 to 12 years old.

Depicted in FIGS. 5 and 6 is a shaping corrective appliance generally used after a treatment using a corrective appliance for transverse expansion. The shaping corrective appliances generally have the function of stabilizing the corrections obtained or of reestablishing correct occlusal equilibrium, in the case of degradation of the periodontium (or polymicrotrauma), provided that this degradation of the periodontium has not reached too advanced a stage.

This appliance comprises, in general, an internal vertical strip (lingual and palatine) and an external vertical strip (vestibular), these two strips being connected by a horizontal plane, i.e. the thick horizontal partition.

As the appliance described is intended for an adult, the length of the rectilinear tooth channel (4) intended to receive the lower incisors is 24 mm.

The two trays of this appliance are dimensioned to cover:

- the upper maxiular arch as far as the boundary between the gum and the inner lip, without resting on the mucosa in order to avoid injuring them;
- the mandibular arch as far as the neck.

Furthermore, the palatine wall advantageously extends beyond the neck of the teeth so as to exert slight pressure on the palate.

Of course, the invention is not restricted to the two groups of corrective appliances described hereinabove. In particular, it also encompasses:

- corrective appliances for retromorphosis, intended to correct class-II anomalies in the shape of the buccal osseous bases (mandible set back relative to the maxilla);
- functional corrective appliances for antemorphosis intended to correct class-III anomalies in the shape of the buccal osseous bases (mandible jutting forward relative to the maxilla), often associated with underdevelopment of the maxilla.

What is claimed is:

1. A corrective appliance for functional dento-facial orthopaedic treatment and periodontics, made of a natural or synthetic flexible and food-grade material, comprising a double channel, these two channels, externally, in a vertical sectional plane, adopting the shape of a flared U and being separated by a thick slightly horizontal partition, the interior surface of these two channels, which are defined between lateral walls among which the vestibular strip and the lingual and palatine strips or rolls and the thick horizontal partition, being smooth, the corrective appliance being characterized in that:

(a) that part of the channel that is intended to receive the lower incisors is in the shape of a straight channel which opens, at its two ends, into two tooth channels respectively, these being intended to receive the lower teeth other than the lower incisors;

(b) the length of the straight channel is designed to be long enough for the four lower incisors to have enough space to fit in it, (c) the depth of the straight channel is designed to completely enclose the lower incisors and, for this purpose, the height of the lingual and vestibular side walls delimiting the straight channel from the thick horizontal partition is at least equal to the height of the incisors up to their neck.

2. A corrective appliance according to claim 1, characterized in that it comprises flexible rubber.

3. A corrective appliance according to claim 2, characterized in that it comprises vulcanized flexible rubber.

4. A corrective appliance according to claim 1, characterized in that the appliance is flavored.

5. A corrective appliance according to claim 1, characterized in that the width of the channel receiving the lower incisors, in its upper part, is designed to be slightly equal to the thickness of the lower incisors in the sagittal direction.

6. A corrective appliance according to claim 1, characterized in that the length of the tooth channel intended to receive the lower incisors is such that the length of this channel is of the order of 20 mm±2 mm.

7. A corrective appliance according to claim 1, characterized in that part of the tooth channel that is intended to receive the upper incisors is laterally delimited by a slightly rounded vestibular wall portion and a planar palatine wall portion in the region of the tooth channel.

8. A corrective appliance according to claim 1, characterized in that the thickness of the horizontal partition is greater in the region of the incisors than the thickness of this same horizontal partition in the region of the other teeth.

9. A corrective appliance according to claim 8, characterized in that the thickness of the horizontal partition in the region of the incisors varies between 2 and 5 mm.

10. A corrective appliance according to claim 1, characterized in that the length of the tooth channel intended to receive the lower incisors is such that the length of this channel is of the order of 22 mm±2 mm.

11. Corrective appliances according to claim 1, characterized in that the length of the tooth channel intended to receive the lower incisors is such that the length of this channel is of the order of 24 mm±1 mm.

* * * * *